United States Patent [19]

McLean et al.

[11] 4,064,311

[45] Dec. 20, 1977

[54] PRODUCTION OF METAL-CERAMIC ARTICLES

[75] Inventors: John Walford McLean, London; Ian Robert Sced, Staines, both of England

[73] Assignee: National Research Development Corporation, England

[21] Appl. No.: 594,324

[22] Filed: July 9, 1975

[30] Foreign Application Priority Data

July 12, 1974 United Kingdom .............. 30978/74
Jan. 8, 1975 United Kingdom .............. 00804/75

[51] Int. Cl.$^2$ ......................... A61C 5/08; B32B 15/04
[52] U.S. Cl. ...................................... 428/434; 32/12;
204/37 T; 204/38 A; 204/38 C; 204/43 G;
204/43 N; 206/524.1; 156/89; 428/472;
428/539; 428/647; 428/648
[58] Field of Search .................. 32/12; 29/199, 196.4;
206/84, 524.1–524.9; 156/89, 428, 204;
428/472, 469, 457, 539, 434, 497, 647, 648;
204/43 G, 43 N, 35 R, 37 T, 38 A, 38 C, 42

[56] References Cited

U.S. PATENT DOCUMENTS

| | | | |
|---|---|---|---|
| 1,195,090 | 8/1916 | Robertson | 428/497 X |
| 1,659,757 | 2/1928 | Aderer | 29/199 |
| 2,399,094 | 4/1946 | Brown et al. | 29/199 X |
| 2,421,719 | 6/1947 | Simmons | 428/529 X |
| 2,975,078 | 3/1961 | Rayfield | 428/469 X |
| 2,980,998 | 4/1961 | Coleman et al. | 32/12 |
| 3,052,983 | 9/1962 | Weinstein et al. | 32/12 |
| 3,222,266 | 12/1965 | Page | 204/42 X |
| 3,422,535 | 1/1969 | Johnson | 32/12 |
| 3,481,772 | 12/1969 | MacNairn et al. | 428/457 X |
| 4,004,057 | 1/1977 | Hoffman et al. | 428/469 |

*Primary Examiner*—Harold Ansher
*Attorney, Agent, or Firm*—Jacobs & Jacobs

[57] ABSTRACT

A process for the production of a metal-ceramic article which comprises firing porcelain on to a metal substrate, the metal substrate having deposited thereon an adherent layer of a metal oxide which is wetted by the porcelain in the fused state.

15 Claims, No Drawings

PRODUCTION OF METAL-CERAMIC ARTICLES

This invention relates to metal-ceramic articles, and more particularly to metal-ceramic tooth restorations.

Porcelain is widely used for the manufacture of tooth restorations, for example jacket crowns, bridges and inlays, because of its high abrasion resistance and aesthetic appeal. In a conventional process for producing porcelain jacket crowns, a platinum foil is swaged around a model of the tooth crown preparation and the porcelain fired thereon. There is little or no adhesion between the platinum and the porcelain, thus permitting the removal of the foil before the finished jacket crown is fitted in the mouth. Where greater strength is required, a specially formulated high fusing gold alloy is cast to fit a model made from an impression of the tooth preparation, forming a coping or insert on to which the porcelain is fired. The composition of the gold alloy is such that a good bond is obtained between the porcelain and the alloy producing a strong composite structure.

For several reasons the present processes are disadvantageous. The particular gold alloys used for dental work are very expensive, and contain trace amounts of base metals which form an oxide scum on casting thus increasing the difficulty of melting and production of clean castings. In addition these alloys cannot be re-used without major additions of fresh metal. The gold alloys are also inclined to creep at the firing temperature of porcelain, necessitating the use of thick sections which increases the cost of the materials and requires the removal of more of the supporting tooth. In addition, aluminous porcelains, which have the highest strength but a low linear coefficient of thermal expansion, cannot be used for metal-ceramic tooth restorations because of the danger of cracking due to the difference between the linear coefficients of thermal expansion of the gold alloy and the porcelain. Special high expansion porcelains are produced for metal-ceramic tooth restorations but the mechanical properties of these materials are greatly inferior to those of aluminous porcelain. These high expansion porcelains also contain a high soda content which increases the risk of devitrification on firing and cloudiness in the porcelain. Attempts to use base metals in place of the gold alloy have been unsuccessful due to the low strength of the porcelain-metal bond, and the discolouration produced by the absorption of base metal ions into the porcelain.

According to the present invention a process has now been developed which may permit the firing of porcelain on to a variety of metal substrates.

The present invention provides a process for the production of a metal-ceramic article which comprises firing porcelain on to a metal substrate, the metal substrate having deposited thereon an adherent layer of a metal oxide which is wetted by the porcelain in the fused state.

The porcelain may, for example, be a dental porcelain, such as those described in "The Science of Dental Materials" by Skinner and Phillips, Chapter 31 page 517 et seq 6th edition. Most preferably, however, the porcelain as described in British Pat. No. 1,105,111. The preferred aluminous porcelains contain from about 40% to about 50% by weight of recrystallised alumina particles of a size classification of less than about 25 microns, the remainder being the glass-forming component which usually consists principally of feldspar, glass fluxes and various metallic pigments.

A variety of metals and alloys may be used as the substrate in the present invention. The most preferred metal substrates are those that do not naturally form a substantial surface coating of oxide at temperatures up to and including the porcelain firing temperature, for example the noble metals such as platinum, rhodium, gold and silver. Excellent results have been obtained with platinum and this is the preferred metal substrate.

The porcelain and metal substrate should preferably be chosen so as to have very similar, if not identical, linear coefficients of thermal expansion in order to minimise the risk of cracking during firing. For example, the expansion coefficient of platinum is $9.7 \times 10^{-6}/°$ C., which is sufficiently close to the expansion coefficient of aluminous porcelain (6.8 to $8.7 \times 10^{-6}/°$ C.) to permit a good bond to be obtained.

The metal oxide may be deposited on the surface of the substrate in any manner suitable for obtaining a thin adherent layer, but in most if not all cases, it will be preferable to deposit a metal layer and then oxidise this to produce the metal oxide. The metal layer may, for example, be produced by vapour deposition, but preferably it is produced by electrodeposition from an appropriate plating solution. Electrodeposition provides a greater degree of control over the deposition process and can provide a more tightly adherent deposited metal layer. It is important to obtain the minimum thickness of deposited metal layer, consistent with adequate coverage of the substrate, and a layer of thickness less than 20 microns is usually sufficient. Preferably the deposited metal layer has a thickness of from 0.2 to 2.0 microns, and most preferably from 0.5 to 1.0 micron. The use of thicker metal layers may result in diffusion of excessive numbers of deposited metal atoms from the surface of the substrate to the interior during subsequent firing, with deleterious effects upon the mechanical properties of the substrate, or the production of an excessive thickness of metal oxide leading to poor adhesion of the porcelain.

The metal which is deposited on to the substrate is one that has an oxide which is wetted by the porcelain to be used, whilst the porcelain is in the fused state. In addition, the metal should preferably be one that diffuses into the substrate on heating with the minimum effect upon the linear coefficient of thermal expansion of the substrate. Its oxide should preferably be one that can dissolve in the glass phase during the firing of the porcelain, without appreciably altering the linear coefficient of thermal expansion of the porcelain, and without reducing or devitrifying the porcelain, or itself being reduced, under the firing conditions. The oxide preferably has a low contact angle with the porcelain whilst the porcelain is in the fused state, and this is normally less than 90° and preferably less than 30°. For dental applications the metal and its oxide should not form coloured compounds with the porcelain and should be biologically compatible. It has been found that certain metals having atomic numbers of from 26 to 50 conform to the above requirements and these are the preferred metals for use in the present invention. Of these the most preferred are tin and indium, although other usable metals include copper, zinc, and nickel. Alloy layers comprising two or more of these metals may also be used. Other potentially useful metals include cobalt for applications where colour is not a limiting factor, and iron. Metals having oxides that are very volatile or that dissociate at the porcelain firing temperature are not preferred as they tend to cause excessive porosity in the porcelain.

Any suitable plating solution having good throwing power may be used to electrodeposit the metal layer upon the substrate, for example tin may be deposited using an alkaline stannate solution, or a solution of tin sulphate containing citric acid or cresol sulphonic acid. Indium may also be deposited from sulphate solutions. For alloy deposition it is likely that complex solutions will be necessary. These may be based, for example, on oxalates, fluoroborates, cyanides or pyrophosphates.

With the very thin deposited metal layers used in the present invention, some diffusion of metal atoms into the substrate can be advantageous in producing a more tightly adherent oxide layer and the substrate is therefore preferably heated in a vacuum or under an inert atmosphere after deposition of the metal layer in order to promote diffusion.

The metal layer is then converted to the oxide, preferably by heating in air or oxygen, although this conversion may also be carried out electrolytically, for example, by reversing the polarity and changing the current density during the electrodeposition.

The sequence of operations for the production of a jacket crown using the process of the present invention is as follows:

First, a model of the tooth stump is prepared and a platinum foil swaged around the model to form the substrate upon which the porcelain is fired. Conventionally, platinum foil of thickness 0.001 inch is used for this purpose, but since in this case the platinum foil is to be bonded to the porcelain, any suitable foil of thickness greater than 0.0005 inch may be used, although foil of thickness of at least 0.001 inch to 0.005 inch is preferred, most preferably foil of thickness from 0.002 inch to 0.005 inch, such as for example 0.003 inch. Cracks in porcelain jacket crowns tend to be initiated from the interior surface, and the thicker foil is preferred to give greater creep resistance and rigidity under stress conditions. It has been found that even platinum foil of thickness 0.003 inch can be quite satisfactorily swaged around a tooth impression, if necessary with annealing during the swaging operation.

The platinum foil may, if desired, be supplied with the appropriate metal or metal oxide layer already deposited thereon, or alternatively a metal layer may be electrodeposited on to the swaged foil. If the platinum foil is supplied with a pre-deposited metal or metal oxide layer, care should be taken that the layer is not disturbed during swaging. Metal oxide layers in particular may be quite brittle, although pre-deposited metal layers, of a thickness of from 0.2 to 2.0 microns have been found to be fairly resistant to disturbance by the swaging operation and may represent a convenient way of carrying out the present invention. Platinum foil having a layer of tin deposited thereon has been found to be especially suitable for use in the present invention, and the invention therefore includes, as a new article of manufacture, a platinum foil having a thickness of from 0.001 inch to 0.005 inch and having deposited on at least one surface thereof an adherent layer of tin having a thickness of from 0.2 to 2.0 microns. If desired the tin-coated platinum foil may be supplied as preformed metal copings, which require only a small amount of swaging to fit the tooth impression, and which may be swaged by a hydraulic swaging process.

After swaging, the foil is removed from the impression and, if necessary, a metal layer electrodeposited upon the surface thereof. There may be supplied to the dentist a kit comprising platinum foil of thickness 0.001 inch to 0.005 inch and a plating bath, or the components thereof, suitable for the deposition of the metal on to the substrate. Electrodeposition may be carried out, for example, by making the foil the cathode in an electrolysis cell using, for example, a tin anode and an electrolyte consisting of 0.3M alkaline sodium stannate. Electrodeposition is carried out for a period of from 0.5 to 5 minutes using a current of from 0.01 to 0.04 amp/sq.cm.

The tin-coated platinum foil substrate is then placed in a furnace which is evacuated and heated to a temperature of from 800° to 1000° C. for a period of from 1 to 5 minutes, followed by heating in air from 1 to 3 minutes at the same temperature. There is produced upon the platinum foil substrate a tightly adherent coating of tin oxide. Aluminous porcelain powder, slightly moistened with water, is then built up around the platinum foil substrate and fired in the furnace at a temperature of from 800° to 1100° C. Several fired layers of porcelain, are usually necessary to simulate the tooth structure, and normal practice is to begin with an opaque porcelain layer, followed by one or more translucent porcelain layers, and finally a veneer porcelain.

The invention has many applications in the field of dental restorations. Instead of the platinum foil technique described above, porcelain may be bonded to cast gold or other metal substrates using the process of the invention. Thus the invention can be used to improve the adhesion of conventional high expansion porcelains to high-fusing gold alloys, for example in soldered joint areas of dental restorations. However in many cases the invention can eliminate the use of special gold castings alloys and may also permit porcelain to be fired on to base metals substrates in appropriate circumstances.

Platinum foil for use in the present invention can desirably be supplied lacquered on one surface, which is made the interior surface of the substrate during swaging. After firing, the lacquer is burnt off leaving a small gap for the insertion of the cement necessary to fix the jacket crown to the tooth stump in the mouth.

Although the invention has been specifically exemplified in terms of dentistry, it is to be understood that it is not limited thereto, and the process is of general application in the production of metal-ceramic articles, for example in the manufacture of jewelry, electronic components, and tableware.

The invention is illustrated by the following Examples:

EXAMPLE 1

This Example describes the production of a metal-ceramic tooth crown using a process according to the present invention.

A model of a tooth crown preparation is prepared and a platinum foil of thickness 0.003 inch is swaged around the model. The shaped foil is then removed from the model, sandblasted to produce a matt surface, and then cleaned electrolytically in sodium hydroxide solution. The foil is then washed in water and made the cathode in an electrolysis cell having a tin anode and an electrolyte consisting of 0.3M alkaline sodium stannate. Electrodeposition is carried out for a period of 1 minute using a current of 0.03 amp/cm$^2$. During electrolysis a thin film of tin is built up on the surface of the platinum foil, and after washing with water, the tin-coated platinum foil is placed in a furnace and the furnace evacuated and heated to a temperature of 1,000° C. After remaining at 1,000° C. for 2 minutes, air is introduced into the furnace and oxidation carried out at the same temperature for 1 minute. Aluminous porcelain (Vitadur S manufactured by Vita Zahnfabrik) moistened with water is then applied to the platinum foil and fired at 1,100° C. Further porcelain layers are then applied and fired, building up the tooth structure in the conventional manner.

EXAMPLE 2

The process of Example 1 is repeated except that in this case the metal substrate is a gold alloy cast to fit around the tooth model. The alloy is a number 3 hard casting alloy which typically has the composition:
Gold — 70%
Copper — 10%
Silver — 15%
Palladium — 3%
Platinum — 1%
Zinc — 1%

EXAMPLE 3

This Example describes a test carried out to determine the adhesive strength of a porcelain to platinum substrate bond produced using a process according to the present invention.

Vitadur core porcelain is fired on to one face of a platinum substrate, which has been tin plated as described in Example 1. The porcelain-coated platinum is then bent through approximately 120° with the porcelain on the outside of the bend. A sample of the substrate taken from an area where the porcelain has flaked off is examined in a scanning electron microscope at X600 magnification. It is observed that much of the failure has occurred through the porcelain leaving large areas of porcelain adhering to the platinum, indicating that a good bond has been obtained between the platinum and the porcelain.

EXAMPLE 4

This Example describes the production of a bonded alumina crown using a foil having a pre-deposited metal layer thereon.

A polysulphide elastomeric impression is taken of a standard jacket crown preparation on a central incisor tooth and electroplated dies are prepared in silver from this impression.

Tin electroplated platinum foil of 0.002 inch thickness is then adapted to the jacket crown by a standard technique using a "tinners" joint to secure the cut edges. This foil is then removed from the die and trimmed accurately to the internal line angles of the preparation at the gingival floor.

Untreated platinum foil of 0.001 inch thickness is then laid down on the die to form a standard platinum foil matrix. This foil is trimmed just short of the external cervical margin of the preparation to form a small apron around the preparation.

The tin-coated foil is then slipped over this foil matrix and pushed to position. Re-burnishing with a rubber tipped instrument ensures close adaption. The preparation is now covered by two foils — an inner foil of pure platinum and an outer foil of platinum provided with the tin-plated surface.

The technique of adapting the twin foils can be modified by the operator. For example he can lay down the inner foil of pure platinum first and then adapt the tin-plated foil over it. This method makes removal of the inner foil necessary prior to trimming the tin plated foil at the internal line angles of the preparation.

After the foils have been adapted the outer foil (tin-coated) is oxidised in a furnace at 800° C for 10 minutes. The foil is then cooled and replaced over the inner matrix of pure platinum foil. A slurry of aluminous core porcelain is then applied, using the brush technique of condensation. The core porcelain used is a 45° % by weight alumina crystal-containing dental porcelain such as Vitadur (Vita Zahnfabrik). This porcelain may be further opacified by the addition of 1-2% of zirconium oxide. The first layer of core porcelain is applied thinly and then fired to position at 1050° C for ten minutes. A suitable time/temperature cycle for firing the porcelain is 800° C – 1080° C over 5 minutes in vacuum followed by air-firing at 1050° for 5 minutes. The latter precautions avoid bloating of the ceramic.

After the first firing of the core porcelain any fissuring present in the surface may be filled in with further porcelain at a second firing made at 1050° C for 5 minutes in air.

Dentine and enamel veneer porcelains are then applied by standard procedure to complete the tooth form. The crown is then stained and glazed.

After final glazing the inner foil is stripped out leaving the tin plated foil firmly bonded to the alimina core porcelain.

The use of this "twin foil" technique has the great advantage of improving aesthetics by allowing a porcelain butt fit on the external cervical margin at the same time preventing the propagation of micro-cracks from the internal surface of the crown. In addition the removal of the thin skin of platinum provides space for the luting cement.

EXAMPLE 5

This Example describes the production of a posterior bonded aluminous porcelain crown.

An electro-plated silver die of a posterior crown preparation is covered with two coats of clear dental varnish (De Trey's cavity varnish). Pure platinum foil of 0.002 inch thickness is then adapted to the die using a "tinner's joint". This platinum matrix is identical to the normal porcelain crown matrix except for its additional thickness. The foil may be adapted either by hand burnishing or swaging.

After adaption the foil is removed and sand-blasted with 27μm alumina. A thin coating of tin is then applied by electro-deposition and oxidised as described in Example 1.

After oxidising of the foil the matrix is readapted to the die and alumina core porcelain applied and fired to position as described in Example 1. The crown may then be completed by standard procedure.

In this method, space is provided for the cement by the thickness of varnish applied to the die.

EXAMPLE 6

This Example describes the repair of fractured metal ceramic bridgework.

In the event of the fracture of a metal ceramic bridge, repair of the broken porcelain may only be done if the bridge is removed. This invention enables the replacement of fractured crown units on a bridge to be made with a bonded alumina crown.

The fractured porcelain on the bridge is removed by diamond grinding from the metal. The metal coping is lightly trimmed to reestablish a classical metal coping form and an impression taken of it in polysulphide elastomer. A silver plated model is made from the impression and a bonded aluminous porcelain crown constructed to fit the die. The same technique is used as described in Example 1. This platinum reinforced aluminous porcelain crown may then be cemented to the fractured area of the bridge to effect a permanent and aesthetic repair.

We claim:

1. A process for the production of a metal-ceramic dental restoration, whih comprises fitting porcelain on to a metal substrate selected from the group consisting of the noble metals and alloys thereof, the metal substrate having deposited thereon an adherent layer of a chemically uncombined metal oxide which is wetted by the porcelain in the fused state.

2. A process according to claim 1, in which the porcelain is a dental aluminous porcelain.

3. A process according to claim 1, in which the metal substrate is a platinum metal substrate.

4. A process according to claim 1, in which the metal oxide is an oxide of a metal having an atomic number of from 26 to 50.

5. A process according to claim 1, in which the metal oxide is an oxide of tin or indium.

6. A process according to claim 1, in which the substrate is heated in a vacuum after deposition of the metal layer in order to promote diffusion of deposited metal atoms into the substrate.

7. A process according to claim 1, in which the deposited metal layer is converted to the oxide by heating in air or oxygen.

8. A process according to claim 1 in which the substrate is a platinum metal foil of thickness from 0.001 inch to 0.005. inch.

9. A process according to claim 1, in which the porcelain is fired on to the metal substrate using a firing temperature of from 800° C to 1100° C.

10. A process according to claim 1, in which the substrate is heated under an inert atmosphere after deposition of the metal layer in order to promote diffusion of deposited metal atoms into the substrate.

11. A process according to claim 1, in which the metal oxide layer is produced by depositing a metal layer on the substrate and then oxidising this layer to produce the metal oxide.

12. A process according to claim 6, in which the metal layer is deposited by electrodeposition.

13. A process according to claim 6, in which the deposited metal layer has a thickness of from 0.2 to 2.00 microns.

14. A metal-ceramic dental restoration produced by practicing the process of claim 1.

15. A metal-ceramic article according to claim 14, which comprises a platinum metal substrate having a tightly adherent layer of porcelain fired thereto.

* * * * *